US006177477B1

(12) United States Patent
George et al.

(10) Patent No.: US 6,177,477 B1
(45) Date of Patent: Jan. 23, 2001

(54) PROPOFOL FORMULATION CONTAINING TRIS

(75) Inventors: Mary Mathew George, Maple Shade; Pui-Ho Yuen, Princeton Junction, both of NJ (US); Martin A. Joyce, Pottstown, PA (US)

(73) Assignee: American Home Products Corporation, Madison, NJ (US)

( * ) Notice: Under 35 U.S.C. 154(b), the term of this patent shall be extended for 0 days.

(21) Appl. No.: 09/275,145

(22) Filed: Mar. 24, 1999

(51) Int. Cl.$^7$ ..................................................... A61K 31/05
(52) U.S. Cl. ............................................. 514/731; 514/975
(58) Field of Search ..................................... 514/731, 740, 514/762, 788, 816, 937, 938, 975

(56) References Cited

U.S. PATENT DOCUMENTS

| | | | |
|---|---|---|---|
| 4,452,817 | * 6/1984 | Glen et al. | 514/730 |
| 5,504,113 | * 4/1996 | Lucero | 514/554 |
| 5,633,240 | * 5/1997 | Ranade | 514/155 |
| 5,637,625 | * 6/1997 | Haynes | 514/731 |
| 5,714,520 | * 2/1998 | Jones et al. | 514/731 |
| 5,962,536 | * 10/1999 | Komer | 514/731 |
| 6,028,108 | * 2/2000 | George | 514/564 |

FOREIGN PATENT DOCUMENTS

98/53805 * 12/1998 (WO).

OTHER PUBLICATIONS

The Merck Index, An Encyclopedia of Chemicals and Drugs. Ninth Edition. 1978. p. 1253.*
Angus Chemical Co., Buffalo Grove, IL, Technology Review, Pharmaceutical. Applications of Tris–Amino, 10–13 and 15.
L. W. Tjoelker et al., J. Dairy Sci., vol. 68, Suppl. 1, 196 (1985).
Angus Chemical Co., Buffalo Grove, IL, Antimickrobial System Applications of Tris Buffer, 1995 Annual Meeting Society for Industrial Microbiology, 1–14.

* cited by examiner

Primary Examiner—Robert H. Harrison
(74) Attorney, Agent, or Firm—Rebecca R. Barrett

(57) ABSTRACT

Sterile pharmaceutical compositions parenteral administration containing propofol in an oil-in-water emulsion additionally containing an amount of the preservative tromethamine sufficient to prevent signficant growth of microorganisms for at least 24 hours after extrinsic contamination.

23 Claims, No Drawings

PROPOFOL FORMULATION CONTAINING TRIS

BACKGROUND OF THE INVENTION

The present invention relates to novel oil-in-water emulsion pharmaceutical composition containing 2,6-diisopropylphenol, i.e. propofol.

Propofol is an injectable anesthetic which can be used to induce and maintain general anesthesia and for sedation, for example in intensive care units. There are a number of known propofol formulations. See, for example, UK Patent 1472793, U.S. Pat. Nos. 4,452,817 and 5,714,520. One formulation of propofol is an oil-in-water emulsion.

Sterile propofol formulations, including oil-in-water emulsion formulations of propofol, have been taught to include preservatives to prevent extrinsic contamination. Ideally, the concentration of preservative is kept to a minimum, especially where propofol is administered for the maintenance of general anaesthesia and sedation where such treatment allows for the possibility of significant amounts of preservative being administered to a patient over the course of treatment. In addition, to be effective for the intended purpose, namely the prevention of extrinsic contamination, a preservative should be broad spectrum, i.e. effective against gram negative (such as *Pseudomonas aeruginosa*) and gram positive (such as *Staphylococcus aureus*) bacteria as well as yeast (such as *Candida albicans*) at useful concentrations. Edetate has been taught to be the only preservative which has broad spectrum antimicrobial effect and can be exerted in the aqueous phase without destabilizing the oil-in-water propofol formulation. See, U.S. Pat. No. 5,714,520.

Tromethamine (TRIS) is a known buffering agent and electrolyte. It has also been previously suggested that tromethamine may enhance the antimicrobial effects of EDTA and other agents. Tjoelker, et al., *J. Dairy Science,* 68, Suppl. 1, 196 (1985); Angus Chemical Company, *Technology Review,* p. 10–13. Tromethamine has not been taught to be effective alone as an antimicrobial agent. Furthermore, due to its ionic nature, tromethamine would not be expected to be compatible with an oil-in-water emulsion because ionic compounds and electrolytes are known to destabilize oil-in-water emulsions. See, U.S. Pat. No. 5,714,520.

Despite these and other teachings, it has surprisingly been found that tromethamine is useful as a preservative in an oil-in-water emulsion. Thus, compositions of the present invention are excellent broad spectrum preservatives useful in an oil-in-water emulsion containing propofol.

DESCRIPTION OF THE INVENTION

The invention is a sterile pharmaceutical composition of propofol for parenteral administration comprising an oil-in-water emulsion in which propofol is dissolved in a water-immiscible solvent and is emulsified with water containing tromethamine as a preservative. Preservative is included in an amount sufficient to prevent any significant growth of microorganism for at least 24 hours in the event of extrinsic contamination.

By an oil-in-water emulsion is meant a two-phase system that is in equilibrium and in effect, as a whole, is kinetically stable and thermodynamically unstable.

Prevention of significant growth of microorganisms is meant growth of microorganism which is preferably no more than a 10 fold increase following extrinsic contamination. For purposes of this definition, the contamination is generally about 10 to about 200 colony forming units/ml, at temperatures in the range of about 20° to about 25° C.

Tromethamine as used herein, refers to 2-amino-2-hydroxymethyl-1,3-propanediol, also known as TRIS. Typically tromethamine is present in compositions of the present invention in amounts of no more than about 0.25% by weight. Preferably, tromethamine is present in the range of about 0.15% to about 0.25% by weight. In some embodiments of the present invention tromethamine is present in amounts of about 0.2% by weight. In other embodiments of the present invention, tromethamine is present in amount of about 0.24% by weight.

Compositions of the present invention typically comprise from 0.1 to 5% by weight of propofol and more preferably from 1 to 2% by weight of propofol. In particular, compositions of the present invention comprise 1% or 2% by weight of propofol.

The oil-in-water emulsion may be prepared by dissolving propofol and other oil-soluble ingredients in a water-immiscible solvent, providing an aqueous phase comprising a surfactant and other water-soluble ingredients, and homogenizing the oil and aqueous phases to provide a concentrated emulsion. The concentrated emulsion is, brought to final volume with water and again homogenized. The emulsion may be filtered. Finally, tromethamine is added. Alternatively, tromethamine may be added initially in the aqueous phase. The formulation is sterilized.

The water-inmmiscible solvent is suitably present in an amount that is up to 30% by weight of the composition, more suitably 5–25%, preferably 10–20% and in particular about 10%.

A wide range of water-immiscible solvents can be used in the compositions of the present invention. Typically the water-immiscible solvent is a vegetable oil, for example, soy bean, safflower, cottonseed, corn, sunflower, arachis, castor or olive oil. Preferably the vegetable oil is soy bean oil. Alternatively, the water-immiscible solvent is an ester of a medium or long-chain fatty acid for example a mono-, di-, or triglyceride; or is a chemically modified or manufactured palmitate, a glyceral ester or polyoxyl hydrogenated castor oil. In a further alternative the water-immiscible solvent may be a marine oil, for example cod liver or another fish-derived oil. Suitable solvents also include fractionated oils for example fractionated coconut oil or modified soy bean oil. Furthermore, the compositions of the present invention may comprise a mixture of two or more of the above water-immiscible solvents.

The oil phase, comprising propofol and a water immiscible solvent, is homogenized with an aqueous phase comprising a surfactant to provide a concentrated emulsion. The surfactant may be present in amounts of no more than about 2%, more suitably about 1% to about 2% by weight, and preferably about 1.2% by weight of the composition. Suitable surfactants include synthetic non-ionic surfactants, for example ethoxylated ethers and esters and polypropylene-polyethylene block co-polymers, and phosphatides for example naturally occurring phosphatides such as egg and soya phosphatides and modified or artificially manipulated phosphatides (for example prepared by physical fractionation and/or chromatography), or mixtures thereof. Preferred surfactants are egg and soya phosphatides. Most preferred is egg lecithin.

Tonicity modifiers are compounds which make the composition isotonic with blood. Tonicity modifiers are suitably present in amounts of no more than about 3% by weight, more preferably about 1% to about 2.5% and most suitably about 2.25% by weight of the total composition. Suitable tonicity modifiers include glycerin.

Compositions of the present invention are suitably formulated to be at alkaline pH. In some preferred embodiments the pH ranges from about 8.5 to about 10.0. In more preferred embodiments pH ranges from about 9.5 to about 10.0. If necessary pH may be adjusted by means of alkali such as sodium hydroxide or acid such as hydrochloric acid.

The composition of the present inventions are typically sterile aqueous formulations and are prepared according to conventional manufacturing techniques using, for example, aseptic manufacture or terminal sterilization by autoclaving.

Compositions of the present invention are useful as anaesthetics which includes sedation and induction and maintenance of general anaesthesia. Accordingly in another aspect the present invention provides a method of producing anaesthesia (including sedation and induction and maintenance of general anaesthesia) in warm-blooded animals, including humans, which comprises administering parenterally a sterile aqueous pharmaceutical composition which comprises an oil-in-water emulsion of propofol and tromethamine.

Dosage regimes will be appreciated by those skilled in the art and may vary from patient to patient. Generally, dosage levels of propofol for producing general anesthesia are from about 2.0–2.5 mg/kg for an adult. Dosage for maintenance of anesthesia are generally about 4–12 mg/kg/hr. Sedative effects may be achieved with, for example, a dosage of 0.3–4.5 mg/kg/hr.

The advantages referred to above for including tromethamine in propofol compositions also apply to intravenous fat emulsions which typically are administered, to patients in need thereof, over periods of a day or more. Examples of such intravenous fat emulsions include Intralipid (marketed by Pharmacia), Lipofundin (Braun) and Travamulsion (Baxter). Intralipid, Lipofundin and Travamulsion are all trademarks.

This invention thus provides sterile intravenous fat emulsions which comprise an amount of a preservative consisting essentially of tromethamine, sufficient to prevent significant growth of microorganisms for at least 24 hours, i.e. prevention of greater than a ten fold increase in growth of micro-organism following extrinsic contamination. In particular the present invention provides a sterile, aqueous composition for parenteral administration which comprises an oil-in-water emulsion in which a water-immiscible solvent is emulsified with water containing an amount of preservative consisting essentially of tromethamine, said amount of preservative being sufficient to prevent significant growth of microorganisms for at least 24 hours.

In further aspects of the invention is provided a sterile aqueous composition for parenteral use which comprises an oil-in-water emulsion in which a pharmaceutical agent is dissolved in a water-immiscible solvent and is emulsified with water containing a preservative consisting essentially of tromethamine. Suitable pharmaceutical agents are those that are capable of being administered parenterally in an oil-in-water emulsion and are typically lipophilic. For example, anti-fungal agents, anti-cancer agents, anti-emetics, steroids, agents acting on the central nervous system, barbituates and vitamin preparations. In particular are provided oil-in-water emulsions which are typically administered continuously to a patient in need thereof for an extended period, generally over 12 hours and more typically for a duration of more than 24 hours.

The following examples are illustrative and are not meant to be limiting of the invention.

EXAMPLES

Preparation of Propofol Formulation

TABLE I

| Quantities | |
|---|---|
| Components | % weight |
| propofol | 1.0 |
| soy bean oil | 10.0 |
| egg lecithin | 1.2 |
| glycerin | 2.25 |
| tromethamine | 0.2 |
| sodium hydroxide | qs |
| water for injection | to 100 |

The composition of the present invention is suitably formulated at pH 8.5–10.0.

Preparation

A sterile aqueous oil-in-water emulsion for parenteral administration is prepared as follows:

1. An aqueous phase is prepared by adding glycerin and egg lecithin in water. 2. The oil phase is prepared by adding propofol to the soy bean oil. 3. The oil phase is added to the aqueous phase at 40° C. and homogenized at high pressures greater than 15,000 PSI. 4. The concentrated emulsion is brought to final volume with water and homogenized at high pressure. After the final emulsion is formed, it is filtered and the tromethamine is added. Tromethamine may be added here or in step 1. It is then filled into containers under nitrogen and autoclaved. All processing stages are carried out under nitrogen and weights refer to weight in the final volume.

Oil-in-water emulsion containing 0%, 0.15% or 0.24% tromethamine and 1% propofol may be prepared in a similar manner using the quantities of ingredients as described in Table I and adjusting pH accordingly with sodium hydroxide or hydrochloric acid.

Microbiological Activity

Oil-in-water formulations of 1% propofol (Table I) containing various additives and 0%, 0.15%, 0.2% and 0.24% tromethamine were prepared as described above. Broth cultures of standard USP preservative efficacy test organisms *Staphylococcus aureus* (ATCC 6538), *Pseudomonas aeruginosa* (ATCC 9027) and *Candida albicans* (ATCC 10231) were added to the test formulations at approximately 100 colony forming units per mL. These aliquots are incubated at 20–25° C. and are tested for viable counts of the said organisms after 24 hours. Data for the propofol emulsion formulations are given below. Tromethamine is effective in preventing a no more than 10-fold increase in growth of micro-organisms for at least 24 hours after microbial contamination at concentrations no greater than about 0.25%.

| Example 1 Formulation with no preservative | | |
|---|---|---|
| | $Log_{10}$ CFU/mL | |
| Organism | Initial | 24 hours |
| S. aureus | 1.8 | 3.1 |
| P. aeruginosa | 1.7 | 3.3 |
| C. albicans | 1.9 | >4.8 |

Example 2
Tromethamine 0.15%, pH 9.3 (adjusted with NaOH)

| Organism | Log$_{10}$ CFU/mL | |
|---|---|---|
| | Initial | 24 hours |
| S. aureus | 1.9 | 1.9 |
| P. aeruginosa | 2.0 | 2.0 |
| C. albicans | 2.1 | 2.6 |

Example 3
Tromethamine 0.20% pH 9.3 (adjusted with NaOH)

| Organism | Log$_{10}$ CFU/mL | |
|---|---|---|
| | Initial | 24 hours |
| S. aureus | 1.9 | 2.1 |
| P. aeruginosa | 2.0 | 1.8 |
| C. albicans | 2.1 | 2.6 |

Example 4
Tromethamine 0.24%, pH 9.4 (adjusted with NaOH)

| Organism | Log$_{10}$ CFU/mL | |
|---|---|---|
| | Initial | 24 hours |
| S. aureus | 1.9 | 2.0 |
| P. aeruginosa | 2.0 | 1.7 |
| C. albicans | 2.1 | 2.6 |

Example 5
Tromethamine 0.24%, pH 9.2 (adjusted with HCl)

| Organism | Log$_{10}$ CFU/mL | |
|---|---|---|
| | Initial | 24 hours |
| S. aureus | 1.9 | 1.9 |
| P. aeruginosa | 2.0 | 2.0 |
| C. albicans | 2.1 | 2.7 |

Example 6
Tromethamine 0.24%, pH 8.9 (adjusted with HCl)

| Organism | Log$_{10}$ CFU/mL | |
|---|---|---|
| | Initial | 24 hours |
| S. aureus | 1.9 | 2.1 |
| P. aeruginosa | 2.0 | 2.1 |
| C. albicans | 2.1 | 2.9 |

As shown by the above results, tromethamine is effective in preventing a no more than 10-fold increase in growth in both gram-positive and gram negative strains of bacteria, as well as yeast.

What is claimed is:

1. A sterile pharmaceutical composition for parenteral administration which comprises an oil-in-water emulsion comprising propofol in a water immiscible solvent and an amount of tromethamine, said amounts being sufficient to prevent a no more than ten-fold increase in the growth of microorganisms for at least twenty-four hours after adventitious extrinsic contamination.

2. The sterile pharmaceutical composition of claim 1 comprising not more than about 0.25% by emulsion weight tromethamine.

3. The sterile pharmaceutical composition of claim 1 comprising from about 0.15 to about 0.25% by emulsion weight tromethamine.

4. The sterile pharmaceutical composition of claim 1 comprising not more than about 30% by emulsion weight of a water immiscible solvent.

5. The sterile pharmaceutical composition of claim 1 comprising from about 10% to about 20% by emulsion weight a water immiscible solvent.

6. The sterile pharmaceutical composition of claim 5 where the water immiscible solvent is vegetable oil or ester of a fatty acid.

7. The sterile pharmaceutical composition of claim 6 where the water immiscible solvent is soy bean oil.

8. The sterile pharmaceutical composition of claim 1 wherein the pH is about 8.5 to about 10.0.

9. The sterile pharmaceutical composition of claim 1 comprising about 1% to about 2% propofol.

10. The sterile pharmaceutical composition of claim 1 comprising about 1% propofol.

11. The sterile pharmaceutical composition of claim 1 comprising about 2% propofol.

12. The sterile pharmaceutical composition of claim 1 further comprising a surfactant.

13. The sterile pharmaceutical composition of claim 12 wherein the surfactant is a naturally occuring phosphatide.

14. The sterile pharmaceutical composition of claim 13 wherein the naturally occuring phosphatide is egg lecithin.

15. The sterile pharmaceutical composition of claim 12 wherein the surfactant is a non-naturally occuring phosphatide.

16. The sterile pharmaceutical composition of claim 1 which is isotonic with blood.

17. The sterile pharmaceutical composition of claim 16 which is isotonic with blood by incorporation of glycerin.

18. The sterile pharmaceutical composition of claim 1 wherein the microorganisms include at least *Staphylococcus aureus* ATCC 6538, *Pseudomonas aeruginosa* ATCC9027 and *Candida albicans* ATCC 10231.

19. A sterile pharmaceutical composition in the form of an oil-in-water emulsion comprising:
 a) about 2% by weight of propofol;
 b) about 10% by weight of soy bean oil;
 c) about 1.2% by weight of egg lecithin;
 d) about 2.25% by weight of glycerin;
 e) about 0.2% by weight tromethamine;
 f) sodium hydroxide qs;
 g) water to 100%.

20. A sterile pharmaceutical composition in the form of an oil-in-water emulsion comprising:
 a) about 1% by weight of propofol;
 b) about 10% by weight of soy bean oil;
 c) about 1.2% by weight of egg lecithin;
 d) about 2.25% by weight of glycerin;

e) about 0.2% by weight tromethamine;

f) sodium hydroxide qs;

g) water to 100%.

21. A sterile intravenous fat emulsion comprising an amount of tromethamine sufficient to prevent an at least ten fold increase in growth of microorganisms for at least 24 hours after extrinsic contamination.

22. A method of preparing a sterile pharmaceutical composition for parenteral administration comprising the steps of:
   a) providing an oil phase comprising a pharmaceutical and a water-immiscible solvent;
   b) providing an aqueous phase comprising a surfactant;
   c) homogenizing the oil phase and aqueous phases to provide a concentrated emulsion;
   d) providing preservative in water;
   e) homogenizing the concentrated emulsion with preservative in water to provide a final emulsion; and
   f) sterilizing the final emulsion.

23. A method of limiting microbial growth in a sterile oil-in-water emulsion pharmaceutical composition following extrinsic contamination of said sterile composition comprising incorporating into said oil-in-water emulsion an amount of tromethamine sufficient to prevent an at least ten fold increase in the growth of microorganisms for at least twenty-four hours after extrinsic contamination.

* * * * *